United States Patent [19]

Abrevaya et al.

[11] Patent Number: 4,962,261

[45] Date of Patent: Oct. 9, 1990

[54] PROCESS FOR UPGRADING METHANE TO HIGHER CARBON NUMBER HYDROCARBONS

[75] Inventors: Hayim Abrevaya, Wilmette; Tamotsu Imai, Mount Prospect, both of Ill.

[73] Assignee: UOP, Des Plaines, Ill.

[21] Appl. No.: 208,910

[22] Filed: Jun. 20, 1988

[51] Int. Cl.$^5$ ............................ C07C 2/00; C07C 5/00
[52] U.S. Cl. ................................. 585/500; 585/525; 585/700; 585/943
[58] Field of Search ............... 585/500, 506, 515, 516, 585/510, 525, 700, 943

[56] References Cited

U.S. PATENT DOCUMENTS

| | | | |
|---|---|---|---|
| 4,507,517 | 3/1985 | Devries et al. | 585/415 |
| 4,567,307 | 1/1986 | Jones et al. | 585/330 |
| 4,658,076 | 4/1987 | Kolts et al. | 585/500 |
| 4,665,259 | 5/1987 | Brazdil et al. | 585/500 |
| 4,721,828 | 1/1988 | Withers et al. | 585/500 |
| 4,734,537 | 3/1988 | Devries et al. | 585/415 |
| 4,777,313 | 11/1988 | Sofranko et al. | 585/500 |
| 4,795,842 | 1/1989 | Gaffney et al. | 585/417 X |
| 4,795,849 | 1/1989 | Gaffney et al. | 585/417 X |
| 4,801,762 | 1/1989 | Leyshon | 585/417 X |
| 4,814,534 | 3/1989 | Devries et al. | 585/407 |
| 4,814,538 | 3/1989 | Devries et al. | 585/407 X |

OTHER PUBLICATIONS

Keller and Bhasin, "Synthesis of Ethylene via Oxidative Coupling of Methane," *Journal of Catalysis*, 73, 9–19, (1982).

*Primary Examiner*—Patrick P. Garvin
*Assistant Examiner*—George R. Fourson
*Attorney, Agent, or Firm*—Thomas K. McBride; John F. Spears, Jr.

[57] ABSTRACT

Methane is upgraded to higher molecular weight hydrocarbons in a process using a novel catalyst comprising boron, tin and zinc. The feed admixture also comprises oxygen. The novel catalyst may comprise one or more Group I-A or II-A elements, preferably potassium.

9 Claims, No Drawings

PROCESS FOR UPGRADING METHANE TO HIGHER CARBON NUMBER HYDROCARBONS

FIELD OF THE INVENTION

The invention relates to a hydrocarbon conversion process. The claimed invention is specifically directed to a catalytic process for upgrading methane to higher carbon number compounds such as ethane, ethylene or propane. The process involves contacting methane with a novel solid heterogeneous catalyst in the presence of oxygen. The novel catalyst contains at least three components and preferably comprises an intimate admixture of boron, tin, zinc and potassium.

PRIOR ART

The economic incentive to convert low value methane to higher hydrocarbons has led to considerable research effort in the area of methane upgrading and the generation of an extensive body of prior art. U.S. Pat. No. 4,734,537 issued to L. Devries and P. R. Ryason is believed to be pertinent for its excellent summary of the prior art of catalytic and noncatalytic processes of methane upgrading and for specific teaching. This reference teaches the use of borides of a wide variety of metals chosen from Groups I-A, II-A, III-A, IV-B or the actinide series. U.S. Pat. No. 4,507,517, also issued to L. Devries and P. R. Ryason, broadly claims the use of boron-containing catalysts in a process for the production of higher molecular weight hydrocarbons from methane. The specific catalysts exemplified in this reference are boron carbide and boron nitride. It appears the processes described in these two references occur without the addition of oxygen to the reaction zone.

U.S. Pat. No. 4,658,076 issued to J. H. Kolts and J. B. Kimble is believed relevant for its disclosure of compositions useful in converting methane to higher hydrocarbons in the presence of free oxygen. The reference presents many different compositions including one comprising a Group I-A metal, such as potassium, zinc or a compound of zinc and optionally a third component chosen from the group consisting of tin, tin compounds and chloride ions. It is believed this reference does not suggest the use of a boron-containing composition.

A different form of methane upgrading process is described in U.S. Pat. No. 4,567,307 issued to C. A. Jones et al. In this process the methane is contacted with an oxide of a metal. To maintain the oxide, the process occurs with pulsed or intermittent flow of oxygen and methane or with circulating solids. The reference indicates the catalyst can comprise a wide variety of materials including a reducible oxide of tin and an alkali or alkaline earth metal. Ethylene produced in this manner is then oligomerized to produce higher hydrocarbons. U.S. Pat. No. 4,721,828 issued to H. P. Withers describes a similar process using a catalyst comprising a reducible iron oxide which may contain an alkali or alkaline earth metal and also one or more metals chosen from a group including tin.

A report on the activity of several metal oxides, including those of tin and boron, was presented by G. E. Keller and M. M. Bhasin in the Journal of Catalysis 73, 9-19 (1982). The oxides were supported on alumina. These materials were tested for the oxidative coupling of methane at atmospheric pressure and temperatures of 500°-1000° C. Tin oxide is considered to be active while boron oxide showed "small activity" above the bare support.

BRIEF SUMMARY OF THE INVENTION

The invention is a novel catalyst and a process for converting methane to a higher molecular weight hydrocarbon via oxidative oligomerization. The process comprises contacting methane and gaseous oxygen with a unique catalyst at conversion conditions. The catalyst preferably comprises boron, tin, zinc and potassium, with the use of potassium being optional. Other compositions are described below.

One embodiment of the invention may be broadly characterized as a process for converting methane to a higher molecular weight hydrocarbon comprising the steps of contacting a feed stream comprising methane with an oxygen source and a catalyst within a reaction zone, with the catalyst comprising catalytically effective amounts of (i) a first component comprising boron, (ii) a second component comprising tin, (iii) a third component comprising one or more elements chosen from the group consisting of zinc, nickel, cobalt and iron and (iv) a fourth component comprising one or more Group I-A or II-A metal, and with the reaction zone being maintained at conversion conditions including a pressure of about 0.5 to 200 atmospheres, a temperature of about 500° to 1500° C. and a methane flow rate of about 50 to 10000 GHSV; and recovering a $C_2$-plus hydrocarbon from an effluent stream withdrawn from the reaction zone.

DETAILED DESCRIPTION

The subject invention finds utility as a process for upgrading methane into more valuable higher molecular weight hydrocarbons. Methane is often produced as a by-product of hydrocarbon conversion processes such as catalytic cracking, hydrocracking, isomerization or catalytic reforming. Large amounts of methane are also recovered or may be recovered from the production of natural gas and crude oil. Methane has only a minimal value as a chemical or petrochemical feedstock and is therefore often consumed by burning. In some instances, the value to be recovered from burning the methane does not justify its transportation or purification, and the methane is simply disposed of by burning in a flare system. In comparison, there is a significant economic value attached to ethane and ethylene and higher aliphatic hydrocarbons. Therefore, there is a significant economic justification for the development of a commercially feasible process for upgrading methane to higher molecular weight hydrocarbons.

There are two required feedstreams in the subject process. The first feedstream will contain methane and will normally contain some impurities such as small amounts of ethane, nitrogen, $CO_2$, etc. The second feedstream to the subject process will comprise a source of oxygen. The second feedstream may therefore comprise air, high-purity oxygen, oxygen-enriched air, or an admixture of oxygen with carbon monoxide and/or carbon dioxide or an admixture comprising oxygen and water. It is important that the second feedstream contains an adequate concentration of oxygen and that it does not contain any material which is poisonous to the catalyst or which is deleterious to the performance of the process. However, the composition of the oxygen supply stream may vary widely as indicated by the above-mentioned possible components. It is preferred that the first feedstream, the methane supply stream, will contain at least 50 mole percent methane. It is also preferred that the oxygen supply stream contains at least 15 mole percent oxygen, with oxygen concentrations greater than 20 mole percent being highly preferred.

The two feedstreams are brought into contact with particles of the subject catalyst in a reaction zone. The configuration of the reaction zone is not a limiting factor upon the process. It is therefore contemplated that the catalyst could be employed in a fixed bed, moving bed, fluidized bed or other suitable arrangement providing adequate contact between the reacting gases and the catalyst particles. The catalyst particles may be in the form of extrudates, spheres, pellets or other particle configurations. The extrudates may be cylindrical or multilobial, meaning they could have a cross section of a clover, star, or other geometric shape. The catalytic composite employed in the subject invention could also be present in the form of a honeycomb or monolith in a fixed bed reactor.

The catalytic material may be supported upon a carrier or base. It is preferred that any such carrier or base material is essentially inert and has no catalytic properties at the conditions employed. Although it is envisioned that the catalytically active materials of the subject invention could be placed upon a support material as through impregnation, it is preferred to employ a wash coating type technique to apply a layer of the catalytic material upon an inert support material. This method of catalyst preparation would be especially preferred in the case of a monolith-type catalyst. Such monoliths would preferably be formed from an inert ceramic material such as magnesium oxide or silica. It is preferred that a catalytic composite, obtained for instance by precipitation, is formed directly into a suitably configured catalytic article. It is contemplated that a superior finished catalyst could be obtained by extrusion with relatively minor amounts (less than 20 weight percent) of inert noncatalytic materials such as binding agents or extrusion aids.

The effluent stream of the reaction zone would typically be at a high temperature which facilitates energy recovery by indirect heat exchange. The effluent stream of the reaction zone will therefore normally be heat exchanged against the feed stream to the reaction zone. This may cool the effluent stream sufficiently to allow its passage into downstream separation or reaction zones. However, it is envisioned that the effluent stream of the reaction zone will be further cooled as by indirect heat exchange against cooling media such as air or cooling water. By-product carbon dioxide present in the reaction zone effluent stream may be removed by scrubbing with a suitable acid gas removal media. For instance, the reaction zone effluent stream could be passed countercurrent to descending aqueous monoethanol amine in a multistage contacting column maintained at adsorption-promoting conditions in order to remove carbon dioxide. The hydrocarbons present in the effluent gas stream may then be recovered at this point by further cooling to effect condensation of the hydrocarbons. The remaining gases would then comprise an admixture of residual oxygen not consumed within the reaction zone, methane not consumed within the reaction zone, nitrogen and other inert gases possibly admixed with either the ethane or oxygen and small amounts of carbon dioxide and carbon monoxide. Depending upon the concentration of methane in the remaining gases, this gas stream could be disposed of as through combustion. Alternatively, any methane could be recovered for recycling to the reaction zone. The hydrocarbons recovered by condensation would normally comprise an admixture of ethane and ethylene plus minor amounts of heavier $C_3$ hydrocarbons. The $C_3$ hydrocarbons would comprise both propane and propylene, but are normally present at low concentrations less than 2 mole percent.

Economic factors may dictate other methods of recovering the product $C_2+$ hydrocarbons from the reaction zone effluent stream. It is envisioned that such other techniques as the use of pressure-swing adsorption or selectively permeable membranes could be employed to recover the products. It is believed that suitable adsorbents would be activated carbon or inorganic oxide molecular sieves of suitable size opening. The hydrocarbons recovered from the reaction zone effluent stream could be passed directly into further separation stages designed to separate olefinic from paraffinic products or could be passed directly into a further reaction zone. For instance, an ethylene-rich stream could be passed into an oligomerization or alkylation reaction zone. The presence of paraffinic homologs to the olefin is often acceptable within an alkylation process, and the presence of other gaseous components of the original reaction zones effluent streams, such as nitrogen, may also be acceptable in an alkylation zone which operates with vapor phase or mixed phase reaction conditions.

The reaction zone is maintained at conversion conditions which promote the conversion of methane to higher molecular weight hydrocarbons. A broad range of such conditions include a pressure of about 0.5 to 200 atmospheres absolute, a temperature of 500° to 1500° C. and a methane flow rate of about 50 to about 10000 gas hourly space velocity (GHSV). A pressure equal to or above 1 atmosphere absolute but below 30 atmospheres is preferred. It is preferred that the reaction zone is maintained at a temperature greater than 700° C. and more preferably within the range of 725° to 1000° C. These specified temperatures refer to the inlet temperature of the reaction zone. Preferably, the maximum temperature experienced within the reaction zone is within 100 Celsius degrees of the inlet temperature. The gas hourly space velocity of the methane through the reaction zone should be above 500. A methane flowrate of about 500 to 6000 GHSV is preferred. More preferably, the gas hourly space velocity of methane through the reaction zone is within the range of from about 1000 to about 5000 $hrs^{-1}$.

The mole ratio of methane and oxygen charged to the reaction zone is believed to be an important variable in achieving acceptable conversion and selectivity. These factors are, of course, also related to the operating conditions and effectiveness and selectivity of the catalyst employed. Because of the variability introduced by these other factors, the mole ratio of oxygen to methane can vary significantly. Therefore, it is contemplated that the process can be operated with a mole ratio of oxygen to methane of from about 0.04:1.0 to about 1.2:1.0. It is preferred that the mole ratio of oxygen to methane is greater than 0.1:1.0. It is also preferred that this mole ratio is less than 1.0:1.0.

The catalyst of the subject invention will preferably comprise at least three separate components and may optionally contain a fourth component. These components are those which are responsible for the catalytic activity or selectivity of the composition as distinguished from support materials or base materials. Such support or base materials will generally be utilized as for providing a particular shape (monolith) or increased external catalyst particle surface area while minimizing the required amount of the active catalytic materials. The components described below therefore do not include alumina, silica-alumina, titania, magnesium oxide, which could be utilized as base or support material.

The first essential component of the catalyst is boron or a boron-containing compound such as a sulfide, halide, oxide, etc. It is preferred that boron is present as an oxide or in an elemental (uncombined) state. The use of halides of boron or of any of the other components of the catalyst is not preferred. The second essential or primary component of the catalyst is tin or a compound containing tin. The tin-containing compound is also preferably an oxide although it could be a sulfide, halide, or other compound.

The third essential catalytic component of the catalyst used in the subject process is one or more metals or compounds containing the metals chosen from the group consisting of zinc, nickel, cobalt, and iron. Again, the third component is preferably present as an oxide but could be present as a different compound. The catalyst may contain a combination of these metals in addition to the boron and tin components. Therefore, the catalyst may contain both zinc and nickel, zinc and cobalt, zinc and iron, nickel and cobalt, iron and cobalt, zinc together with nickel and cobalt or nickel together with cobalt and iron, etc.

As used herein the term "metal compound" is intended to include those containing two or more metals. Therefore, a single compound containing boron, tin and zinc is considered to be within the scope of the subject invention. The third component elements such as zinc and nickel could be physically combined as an alloy or other type of blend which is then admixed or compounded into the structure of the overall catalyst together with the other primary components of the catalyst.

As mentioned above, the three primary components of the catalyst are preferably present as oxides. The metallic components may therefore be linked together via oxygen atoms into a single multimetal oxide. Alternatively, the catalyst can comprise an oxide containing only two primary catalyst components. The catalyst therefore could comprise elemental boron intermixed with an oxide comprising tin and zinc. The catalyst could also comprise elemental boron intermixed with tin oxide or elemental boron intermixed with a mixture of tin oxide and zinc oxide. The catalyst could also comprise an admixture of boron oxide, tin oxide and elemental zinc. A further contemplated composition of the catalyst comprises an admixture of boron oxide together with a mixture of elemental tin and zinc.

A highly specific embodiment of the invention may be characterized as a process for converting methane to ethane and ethylene which comprises contacting a feed stream comprising methane and oxygen in a mole ratio of oxygen to methane of 0.1:1.0 to 1.0:1.0 with a particulate solid catalyst consisting essentially of an unsupported intimate admixture of boron, tin and zinc oxides present in a ratio of elemental components of 1.0 Zn: 0.1-5.0 Sn: 0.1-7.0 B at a pressure of 0.5-200 atmospheres absolute and temperature of 500°-1500° C. and recovering ethane.

The catalyst employed in the subject process will optionally contain a fourth component. The use of this fourth component is preferred. The fourth catalytic component is one or more metals chosen from Groups I-A and II-A of the Periodic Table of the version commonly employed in the United States. The elements in this Group I-A, also referred to as the alkali metals, are lithium, sodium, potassium, rubidium and cesium. The elements in this Group II-A, also referred to as the alkali earth metals, include beryllium, magnesium, calcium, strontium and barium. Preferably, the fourth component is chosen from the group consisting of potassium, cesium and strontium. The catalyst may contain a mixture of two or more elements or compounds of the elements of Groups I-A and II-A. Therefore, the catalyst may comprise both potassium and calcium, potassium and strontium, potassium and cesium, calcium and cesium, calcium and barium, magnesium and calcium, sodium and barium, and potassium and strontium, etc. It is contemplated that the fourth component can be utilized in conjunction with any of the combinations of the three primary catalyst components set out above. The catalyst may therefore comprise an admixture of compounds or elemental components such as boron, tin, zinc and potassium; boron, tin, zinc and sodium; boron, tin, zinc and cesium; boron, tin, zinc and strontium; boron, tin, zinc, potassium and barium; boron, tin, zinc, potassium and calcium; boron, tin, zinc, potassium and magnesium; or boron, tin, zinc, and magnesium.

Other possible combinations of catalytic components contemplated for the subject catalyst and for use in the subject invention include boron, tin, nickel and potassium; boron, tin, cobalt and potassium; boron, tin, iron and potassium; boron, tin, zinc, iron and potassium; boron, tin, zinc, nickel and cesium; etc.

It is preferred that the relative molar ranges of the three primary components of the catalyst used in the subject process are within the ranges of 0.1-7.0 B:0.1-5.0 Sn:1.0 X wherein X represents the third primary component of the catalyst and is chosen from the group consisting of zinc, nickel, cobalt and iron. These ratios are the mole ratios of the elemental metals within the catalyst composite. The subject invention may accordingly be characterized as a process for converting methane to $C_2$ plus hydrocarbons which comprises contacting a feed admixture comprising methane and oxygen with a catalyst at conversion conditions and recovering an effluent stream comprising ethane, with said catalyst comprising a solid composite having a composition expressed in terms of mole ratios of elemental components of 1.0 Zn:0.1-5.0 Sn:0.1-7.0 B.

The catalytic composite employed in the subject process preferably comprises a smaller amount of the optionally fourth catalytic component than it does of the other three components. A general range of the mole ratios of boron to the fourth component may be expressed as 1.0 B:0.01-0.5 Y, wherein Y stands for the Group-I or Group-II metal as characterized above.

The catalyst employed in the subject process is preferably free of any zeolitic material and therefore will preferably not contain any appreciable amounts of mordenite, ZSM-5 type zeolites, or zeolite X or zeolite Y, etc.

A catalyst useful in the subject process was prepared using a precipitation technique. An aqueous solution was prepared containing 224 grams $SnCl_4.5H_2O$ plus 380 grams $Zn(NO_3)_2.6H_2O$ in a total solution volume of 1.5 liters. This was added to a preparation consisting of 600 grams of 29 percent aqueous ammonia in one liter of water. Stirring was maintained for 20 minutes after addition was complete. The product of the precipitation was filtered. The product of the precipitation was again suspended in water and slurried in a wearing blender. The material was then filtered. This procedure was repeated twice after the initial precipitation and filtering. The product was then suspended in water containing 0.6 moles of boric acid and again slurried in the water. The resulting material was then heated over steam to evaporate off water. The product was then dried in an oven at 250° F. (121° C.) and split into equal parts by weight. The material was then calcined in an oven for 16 hours at 650° C. The material produced by calcining was then ground and separated to obtain a 20-40 Tyler mesh size range material.

methane and air fed to the reaction zone. The reaction zone was operated at a gas hourly space velocity based upon methane charged to the reactor of 1500 $hr^{-1}$ at a temperature as indicated in the Table and at a total pressure of 1 atmosphere absolute. In each instance, 25 grams of the catalyst was retained between two horizontal screens in a vertical reaction tube surrounded by electric heating elements. The feed gas was passed downward through the reaction tube and the catalyst. The reaction products of ethane, ethylene, higher hydrocarbons, carbon dioxide, carbon monoxide and water together with any residual feed components were analyzed by gas chromatography.

CATALYST TEST RESULTS

| Sample No. | Composition Mole Ratios | Temperature °C. Inlet | Temperature °C. Maximum | Conversion $C_1$ | Conversion $O_2$ | Selectivity $C_2/C_2^=$ | Selectivity CO | Selectivity $CO_2$ |
|---|---|---|---|---|---|---|---|---|
| 1 | 0.94B/2Sn/1Zn | 775 | 798 | 7.1 | 34 | 54 | 14 | 32 |
| 2 | 0.94B/2Sn/1Zn | 775 | 794 | 8.4 | 45 | 38 | 22 | 40 |
|   |   | 790 | 809 | 10 | 49 | 45 | 18 | 37 |
| 3 | 0.94B/2Sn/1Zn/0.05K | 775 | 784 | 7.2 | 32 | 63 | 10 | 27 |
|   |   | 790 | 802 | 10 | 45 | 60 | 13 | 27 |
| 4 | 1Sn/2Zn | 708 | 855 | 12.1 | 100 | 12 | 0 | 88 |
|   |   | 782 | 932 | 11.8 | 100 | 11 | 80 |   |
| 5 | 1.5B/1Zn | 778 | 783 | 2.6 | 18 | 43 | 22 | 35 |
| 6 | 1B/1Zn/3α-$Al_2O_3$ | 779 | 786 | 3.5 | 24 | 32 | 42 | 26 |
| 8 | 1Sn/1Zn/7.2α-$Al_2O_3$ | 583 | 774 | 9.9 | 99 | 4 | 0 | 96 |
| 9 | 0.94B/2Sn/2Zn | 789 | 797 | 4.6 | 30 | 21 | 29 | 50 |
| 10 | 0.94B/0.5Sn/2Zn | 779 | 779 | 1.4 | 16 | 29 | 43 | 29 |
| 11 | 0.94B/1Sn/4Zn | 775 | 811 | 12 | 64 | 40 | 17 | 43 |
|   |   | 791 | 820 | 12 | 60 | 42 | 18 | 40 |
| 12 | 1.88B/1Sn/2Zn | 775 | 777 | 1.3 | 10 | 28 | 30 | 42 |
|   |   | 789 | 791 | 1.8 | 12 | 28 | 32 | 40 |
| 13 | 0.94B/1Sn/2Zn/0.5K | 775 | 781 | 4.8 | 32 | 40 | 12 | 48 |
| 14 | 0.94B/1Sn/2Zn/0.1K | 775 | 785 | 8.1 | 40 | 58 | 12 | 30 |
|   |   | 790 | 808 | 10.6 | 52 | 58 | 11 | 31 |
| 15 | $BPO_4$ | 773 | 776 | 4.2 | 9.2 | 12 | 80 | 8 |
| 17 | Quartz Chips | 750 | 751 | 1.4 |   | 30 |   |   |
|   |   | 800 | 800 | 1.6 |   | 36 |   |   |
| 18 | ZnO | 702 | 729 | 13.2 | 100 | 1.4 | 9.1 | 86.4 |

The use of small size catalyst particles was preferred for testing to allow or provide sizable amounts of external surface area. The internal surface area or total surface area as provided by a pore structure in this material is normally relatively low. It is preferred that the surface area of the material is within the broad range of from 1 to 20 meters$^2$ per gram. It is believed that large surface areas are indicative of an extensive pore structure which in turn would lead to longer residence time of the reactive hydrocarbons within the catalyst particles. Smaller surface areas, which translates into a smaller pore structure and residence time within the catalyst particle, are preferred to minimize the possibility of side reactions between reaction products and oxygen.

A catalyst made according to the above procedure was tested, with the results being the top entry (sample 1) in Table 1 below. The second catalyst listed in Table 1 (sample 2) was made by a similar method with the exception that aqueous ammonia solution was added to the zinc and tin containing solution. The other catalysts were manufactured using similar precipitation techniques followed by washing and calcination. The catalysts of samples 13 and 14 also differed in that a carbonate salt was used to add potassium to sample 13 while a nitrate was used to add potassium to sample 14. No data is reported for samples 7 and 16 due to analytical problems which lead to suspect data.

The various catalysts were tested in a small scale pilot plant. The test conditions included a 1:1 mole ratio of Sample No. 17 comprised quartz chips which are believed to be essentially inactive as catalysts for this reaction. This test therefore serves as a blank or dummy for the other tests. The yield (defined as conversion times selectivity) of $C_2$-plus products achieved with the quartz chips of Sample No. 17 should therefore be subtracted from the yield obtained with the other materials at equivalent conditions.

One sample which was tested but which is not listed in the Table comprised 10 weight percent boron supported on magnesium oxide (MgO). This test result is not reported as the reactor plugged during testing. It is believed boric oxide is formed and melts. This material flows to the reactor outlet and solidifies in the cooler tubing present at this location.

The materials labeled as Sample Nos. 1, 2, 3, 13 and 14 are within the scope of the present invention. Sample No. 2 was found to have a surface area of 4.9 square meters per gram, while the surface area of Sample Nos. 3 was 4.7 square meters per gram. The material of Sample No. 2 was submitted for x-ray diffraction analysis. This indicated the presence of both tin oxide and a tin zinc compound. The material was also submitted for analysis by ESCA (Electron Spectroscopy for Chemical Analysis). The binding energies for boron, zinc and tin in the sample were lower than those for the corresponding simple oxides ($B_2O_3$, ZnO and $SnO_2$). The x-ray diffraction phases indicated were $SnO_2$, $2ZnO \cdot SnO_2$ and $3ZnO \cdot B_2O_3$.

The data for Sample Nos. 4 and 8 indicate that materials containing tin and zinc gave approximately 100 percent conversion of oxygen. This indicates a lack of selective catalytic activity for materials containing just tin and zinc. In contrast to the tin - zinc compositions, the test results of the Table indicate a boron - zinc composition appears to be both catalytically active and highly selective. It is therefore believed that a boron-zinc compound is an essential catalytic component, and that a highly effective catalyst for the subject process could possibly be formulated containing only boron and zinc and therefore be essentially free of tin. It is postulated that this is evidence that an active catalytic component of the mixed oxides catalyst of the subject invention is a boron - zinc compound or is located at the interphase between boron and zinc atoms or crystallites.

If this postulation is correct, the tin oxide could be serving as a support material for the active boron - zinc catalytic phase. Nevertheless, it may be noted that the activity of the sample materials is normally low without tin being present in the composite. It is therefore believed the presence of tin or a tin oxide within the catalytic composite is beneficial to the overall performance of the catalyst even though the tin may not be an active component of the catalyst. The tin or tin oxide may be serving as a support or catalyst moderator which functions as by improving the surface area or configuration of catalytic sites available to the reactants.

It must be noted that the test results reported in the Table are an indication of a survey of various materials. It is not intended to represent optimized performance of any particular material which was tested. The performance of such an optimized catalyst composition and particle configuration would be expected to exceed that reported in the Table in terms of conversion and/or selectivity. The data, however, does indicate the workability of the process and the utility of the various catalysts disclosed within the Table. The data also does not represent any attempt to optimize performance by selection of the most effective combination of operating conditions of temperature, space velocity, etc.

The calculation of the methane conversion as reported in the Table is calculated as the difference between the percent carbon in the feed methane minus the percent carbon in the product methane divided by the percent carbon in the feed methane. For example, if the feedstream contains 49 mole percent methane, one mole percent ethane, and 50 mole percent air, the percent carbon in the feed methane equals the product of 100 multiplied by 49 divided by 51 or 96.08%. This result is the carbon mole percent for the methane. Selectivity to ethane and ethylene is calculated by dividing the difference between the percent total carbon in the ethane and ethylene in the product minus the percent carbon in the ethane and ethylene in the feed by the percent carbon in the feed methane minus the percent carbon in the product methane.

What is claimed:

1. A process of converting methane to a hydrocarbon having two or more carbon atoms per molecule, which process comprises the steps:
    (a) contacting methane and oxygen with a catalyst consisting essentially of oxides of boron, tin and zinc and optionally potassium or a compound thereof in a reaction zone maintained at conversion conditions, and
    (b) recovering a hydrocarbon having two or more carbon atoms per molecule from an effluent stream of the reaction zone.

2. The process of claim 1 further characterized in that the conversion conditions include a pressure of about 0.5 to 200 atmospheres absolute and a temperature of 725° to 1000° C.

3. The process of claim 2 further characterized in that oxygen is fed to the reaction zone at a mole ratio of oxygen to methane of from about 0.4:1.0 to about 1.2:1.0.

4. The process of claim 1 further characterized in that the catalyst comprises potassium.

5. The process of claim 3 further characterized in that the mole ratios of boron, tin and zinc in the catalyst are within the ranges of 0.1–7.0 B:0.1–5.0 Sn:1.0 Zn.

6. A process for converting methane to $C_2$-plus hydrocarbons which comprises contacting a feed admixture comprising methane and oxygen with a catalyst at conversion conditions and recovering an effluent stream comprising ethane and ethylene, with catalyst consisting essentially of a solid composite of oxides of boron, tin and zinc and optionally potassium or a compound thereof, said composite having a composition expressed in terms of mol ratios of elemental zinc, tin and boron components of: 1.0 Zn:0.1–5.0 Sn:0.1–7.0 B.

7. The process of claim 6 further characterized in that the conversion conditions comprise a pressure of about 0.5 to 200 atmospheres absolute, a temperature above 700° C. and a methane flow rate of about 50 to 1000 GHSV.

8. The process of claim 7 further characterized in that the oxygen is present in the feed admixture at a mole ratio of oxygen to methane of about 0.04:10 to about 1.2:1.0.

9. A process for converting methane to ethane and ethylene which comprises contacting a feed stream comprising methane and oxygen in a mol ratio of oxygen to methane of 0.1:1.0 to 1.0:1.0 with a solid catalyst consisting essentially of an intimate admixture of boron, tin and zinc oxides and optionally potassium or a compound thereof, said oxides being present in a ratio of elemental components of 1.0 Zn: 0.1–5.0 Sn:0.1–7.0 B, said contacting occurring at a pressure of 0.5–200 atmospheres absolute and temperatures of 500°–1500° C., and recovering ethane and ethylene.

* * * * *